(12) United States Patent
Stadler et al.

(10) Patent No.: US 11,331,035 B2
(45) Date of Patent: May 17, 2022

(54) RECOVERY OF CARDIAC EVENT SENSING AND RHYTHM DETECTION FOLLOWING ELECTRICAL STIMULATION PULSE DELIVERY

(71) Applicant: Medtronic, Inc., Minneapolis, MN (US)

(72) Inventors: Robert W. Stadler, Shoreview, MN (US); Jian Cao, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 280 days.

(21) Appl. No.: 16/531,685

(22) Filed: Aug. 5, 2019

(65) Prior Publication Data

US 2019/0351246 A1 Nov. 21, 2019

Related U.S. Application Data

(63) Continuation of application No. 14/519,220, filed on Oct. 21, 2014, now Pat. No. 10,369,372.

(51) Int. Cl.
  *A61N 1/39* (2006.01)
  *A61B 5/363* (2021.01)
  *A61N 1/37* (2006.01)
  *A61B 5/349* (2021.01)
  *A61B 5/361* (2021.01)

(52) U.S. Cl.
  CPC ............ *A61B 5/363* (2021.01); *A61N 1/3956* (2013.01); *A61N 1/3987* (2013.01); *A61B 5/349* (2021.01); *A61B 5/361* (2021.01); *A61N 1/3702* (2013.01); *A61N 1/3925* (2013.01); *A61N 1/39622* (2017.08)

(58) Field of Classification Search
None
See application file for complete search history.

(56) References Cited

U.S. PATENT DOCUMENTS

| | | |
|---|---|---|
| 5,018,522 A | 5/1991 | Mehra |
| 5,117,824 A | 6/1992 | Keimel et al. |
| 5,269,300 A | 12/1993 | Kelly et al. |

(Continued)

FOREIGN PATENT DOCUMENTS

| | | |
|---|---|---|
| CN | 1342094 A | 3/2002 |
| CN | 101583397 A | 11/2009 |

OTHER PUBLICATIONS (PCT/US2015/054357) PCT Notification of Transmittal of the International Search Report and the Written Opinion of the International Searching Authority, dated Jan. 4, 2012, 12 pages.

(Continued)

*Primary Examiner* — Erica S Lee
(74) *Attorney, Agent, or Firm* — Shumaker & Sieffert, P.A.

(57) ABSTRACT

A medical device is configured to deliver an electrical stimulation pulse to a heart of a patient, determine a pre-stimulation cardiac event amplitude prior to delivering the electrical stimulation pulse and adjust a cardiac event sensing threshold according to a first post-stimulation decay sequence in response to the electrical stimulation pulse delivery. The first post-stimulation decay sequence is controlled by a sensing module of the medical device according to a first set of sensing control parameters including at least one sensing control parameter based on the pre-stimulation cardiac event amplitude.

20 Claims, 6 Drawing Sheets

(56) References Cited

U.S. PATENT DOCUMENTS

| | | |
|---|---|---|
| 5,339,820 A | 8/1994 | Henry et al. |
| 5,354,316 A | 10/1994 | Keimel |
| 5,447,519 A | 9/1995 | Peterson |
| 5,545,186 A | 8/1996 | Olson et al. |
| 5,545,189 A | 8/1996 | Olson et al. |
| 5,645,569 A | 7/1997 | Ayers |
| 5,658,317 A | 8/1997 | Haefner et al. |
| 5,676,687 A | 10/1997 | Ayers |
| 5,891,048 A | 4/1999 | Nigam et al. |
| 6,157,859 A | 12/2000 | Alt |
| 6,249,701 B1 | 6/2001 | Rajasekhar et al. |
| 6,295,470 B1 | 9/2001 | Mower |
| 6,377,851 B1 | 4/2002 | Shieh et al. |
| 6,393,316 B1 | 5/2002 | Gillberg et al. |
| 6,745,068 B2 | 6/2004 | Koyrakh et al. |
| 7,031,771 B2 | 4/2006 | Brown et al. |
| 7,353,062 B2 | 4/2008 | Kim et al. |
| 7,392,081 B2 | 6/2008 | Wagner et al. |
| 7,496,408 B2 | 2/2009 | Ghanem et al. |
| 7,496,409 B2 | 2/2009 | Greenhut et al. |
| 7,570,997 B2 | 8/2009 | Lovett et al. |
| 7,593,771 B2 | 9/2009 | Younce et al. |
| 7,610,087 B2 | 10/2009 | Ohman et al. |
| 7,991,470 B2 | 8/2011 | Kim et al. |
| 8,160,684 B2 | 4/2012 | Ghanem et al. |
| 8,214,038 B2 | 7/2012 | Kim et al. |
| 8,301,233 B2 | 10/2012 | Zhang et al. |
| 8,332,022 B2 | 12/2012 | Brown et al. |
| 8,437,842 B2 | 5/2013 | Zhang et al. |
| 8,483,841 B2 | 7/2013 | Sanghera et al. |
| 9,042,980 B2 | 5/2015 | Ostroff et al. |
| 9,682,244 B2 | 6/2017 | Stadler et al. |
| 10,369,372 B2 | 8/2019 | Stadler et al. |
| 2002/0147468 A1 | 10/2002 | Kim et al. |
| 2004/0015197 A1 | 1/2004 | Gunderson |
| 2007/0055314 A1 | 3/2007 | Bardy et al. |
| 2008/0275516 A1 | 11/2008 | Ghanem et al. |
| 2009/0157128 A1* | 6/2009 | Seim .................. A61N 1/3621 607/4 |
| 2009/0228057 A1 | 9/2009 | Allavatam et al. |
| 2013/0261473 A1* | 10/2013 | Xi .................. A61B 5/0215 600/486 |
| 2014/0107718 A1 | 4/2014 | Foote et al. |
| 2016/0106991 A1 | 4/2016 | Stadler et al. |

OTHER PUBLICATIONS

First Office Action and Search Report, and translation thereof, from counterpart Chinese Application No. 201580057183.3, dated Sep. 30, 2019, 11 pp.

Prosecution History from U.S. Appl. No. 14/519,220, dated Feb. 23, 2016 through Jun. 20, 2019, 298 pp.

* cited by examiner

RECOVERY OF CARDIAC EVENT SENSING AND RHYTHM DETECTION FOLLOWING ELECTRICAL STIMULATION PULSE DELIVERY

CROSS REFERENCE

This application is a continuation application of and claims priority to U.S. application Ser. No. 14/519,220, filed on Oct. 21, 2014 (published as U.S. Pat. Pub. No. 2016/0106991), which is hereby incorporated by reference herein in its entirety.

TECHNICAL FIELD

The disclosure relates generally to implantable medical devices and, in particular, to a method and apparatus for sensing cardiac signals and detecting a cardiac rhythm following delivery of an electrical stimulation pulse to a patient's heart.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, e.g., implanted in the heart through one or more veins. Other leads may be non-transvenous leads implanted outside the heart, e.g., implanted epicardially, pericardially, or subcutaneously. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal cardiac rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for recovering cardiac signal sensing after delivery of an electrical stimulation pulse to a patient's heart, such as a cardioversion (CV) or defibrillation (DF) shock. An implantable cardioverter defibrillator (ICD) operating in accordance with the techniques of this disclosure performs post-stimulation cardiac signal sensing that is modified from pre-stimulation cardiac signal sensing. A cardiac event sensing threshold for sensing cardiac electrical signals is automatically adjusted according to a post-stimulation decay sequence after electrical stimulation pulse delivery. The post-stimulation decay sequence is based, at least in part, on a pre-stimulation cardiac event amplitude determined prior to delivering an electrical stimulation pulse.

In one example, the disclosure provides a method comprising delivering an electrical stimulation pulse to a heart of a patient; determining a pre-stimulation cardiac event amplitude prior to delivering the electrical stimulation pulse; and automatically adjusting a cardiac event sensing threshold according to a first post-stimulation decay sequence in response to the electrical stimulation pulse delivery wherein the first post-stimulation decay sequence is controlled by a first set of sensing control parameters comprising at least one sensing control parameter based on the pre-stimulation cardiac event amplitude.

In another example, the disclosure provides a medical device comprising a therapy delivery module configured to generate and deliver a an electrical stimulation pulse to a patient's heart via a plurality of electrodes coupled to the medical device; a sensing module configured to receive a cardiac electrical signal and produce cardiac event signals in response to the cardiac electrical signal crossing a cardiac event sensing threshold; a control module coupled to the sensing module and the therapy delivery module and configured to receive the cardiac event signals from the sensing module and control the therapy delivery module to deliver the electrical stimulation pulse, determine a pre-stimulation cardiac event amplitude prior to delivery of the electrical stimulation pulse; the sensing module further configured to adjust a cardiac event sensing threshold according to a first post-stimulation decay sequence in response to delivery of the electrical stimulation pulse by the therapy delivery module, the first post-stimulation decay sequence controlled by a first set of sensing control parameters comprising at least one sensing control parameter based on the pre-stimulation cardiac event amplitude.

In another example, the disclosure provides a non-transitory, computer-readable storage medium comprising instructions that, when executed by a control module in a medical device, cause the medical device to deliver an electrical stimulation pulse to a heart of a patient; determine a pre-stimulation cardiac event amplitude prior to delivering the electrical stimulation pulse; and adjust a cardiac event sensing threshold according to a first post-stimulation decay sequence in response to the electrical stimulation pulse delivery, the first post-stimulation decay sequence controlled by a first set of sensing control parameters comprising at least one sensing control parameter based on the pre-stimulation cardiac event amplitude.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
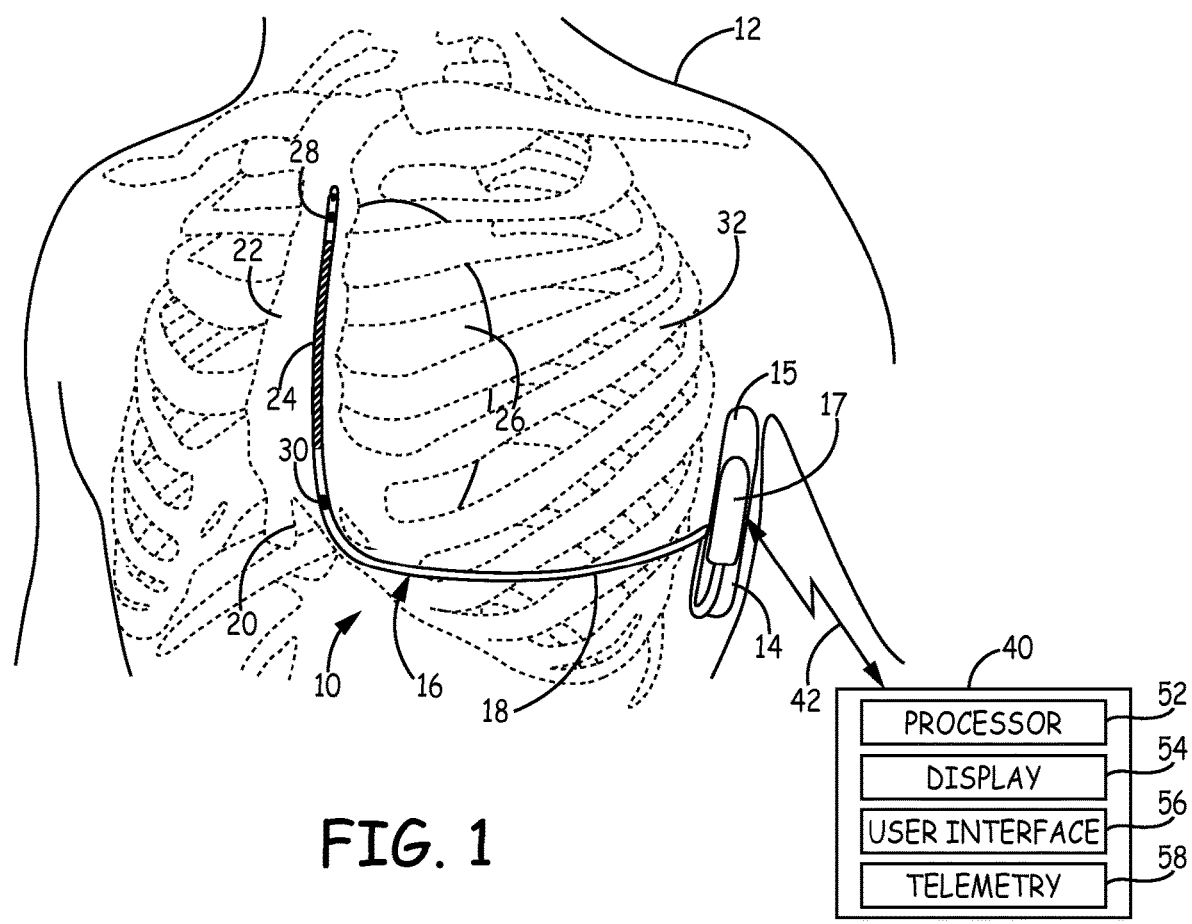
FIG. 1 is a conceptual diagram of a patient implanted with an example IMD system that includes an ICD coupled to a subcutaneous defibrillation and sensing lead.

In general, this disclosure describes techniques for sensing cardiac events for distinguishing between shockable arrhythmias and non-shockable arrhythmias. Shockable arrhythmias refer to abnormal heart rhythms for which a shock therapy is delivered to one or both of the ventricles. Shockable arrhythmias may include ventricular tachycardia (VT) and ventricular fibrillation (VF). Shockable arrhythmias generally pose an immediate danger to the patient and therapy is needed in order to ensure the safety of the patient. Non-shockable arrhythmias, on the other hand, refer to normal or abnormal heart rhythms that typically do not require a shock therapy to be delivered to either of the ventricles or a paced rhythm by another implanted pacemaker. Non-shockable cardiac rhythms may include supraventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-shockable arrhythmias do not generally pose an immediate danger to the patient. As such, non-shockable arrhythmias may go untreated, i.e., no shock therapy is delivered to the heart. In other instances, non-shockable arrhythmias may be treated using an electrical stimulation therapy, but the electrical stimulation therapy may be a low-voltage pacing therapy or is not delivered to the ventricles of the patient.

A shock therapy generally includes at least one a high-voltage shock pulse, which may be in the range of at least 10 Joules and up to 35 Joules for transvenous lead systems carrying intracardiac cardioversion/defibrillation electrodes and in the range of at least 65 Joules and up to 80 Joules for subcutaneous lead systems carrying extracardiac cardioversion/defibrillation electrodes. After delivering a shock therapy, accurate determination of whether the shockable rhythm has been terminated is needed so that, if the shockable arrhythmia is not terminated, another shock can be promptly delivered, typically with a higher or maximum shock energy. Additionally, there is a need for rapid assessment of the cardiac electrical activity post-shock to detect the need for post-shock pacing, e.g., to treat cardiac asystole or bradycardia subsequent to CV/DF shock delivery.

Cardiac electrical signals, such as a subcutaneous electrocardiogram (ECG) or an intracardiac electrogram (EGM) are received via implanted electrodes and analyzed by an ICD to detect a shockable heart rhythm. The cardiac electrical signal includes cardiac event signals attendant to the depolarization (e.g., R-waves) and the repolarization (e.g., T-waves) of the ventricles. An ICD according to the present disclosure includes a tachyarrhythmia detection module configured to discriminate between shockable and non-shockable heart rhythms after delivering a shock pulse by analyzing a cardiac electrical signal received during a post-shock signal analysis segment. The ICD includes a sensing module configured to sense cardiac event signals, such as R-waves, using an automatically adjusted post-shock sensing threshold that enables the ICD to rapidly detect a shockable rhythm post-shock. The automatic adjustment of the cardiac event sensing threshold, e.g., an R-wave sensing threshold, is modified post-shock to promote proper detection of low amplitude post-shock fibrillation waves or asystole and rapidly determine the post-shock cardiac rhythm in order to provide an appropriate therapeutic response to the post-shock cardiac rhythm. Although the techniques of this disclosure are described mainly in the context of sensing after delivery of a shock, the techniques may be utilized for rapid sensing recovery after other types of electrical stimulation, including but not limited to post-shock pacing and atrial tachycardia pacing (ATP).

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal end that includes one or more electrodes. Defibrillation lead 16 is illustrated in FIG. 1 as being implanted subcutaneously, e.g., in tissue and/or muscle between the skin and the ribcage 32 and/or sternum 22. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. Although illustrated as being offset laterally from and extending substantially parallel to sternum 22 in the example of FIG. 1, defibrillation lead 16 may be implanted over sternum 22, offset from sternum 22, but not parallel to sternum 22 (e.g., angled laterally from sternum 22 at either the proximal or distal end).

Figure 2:
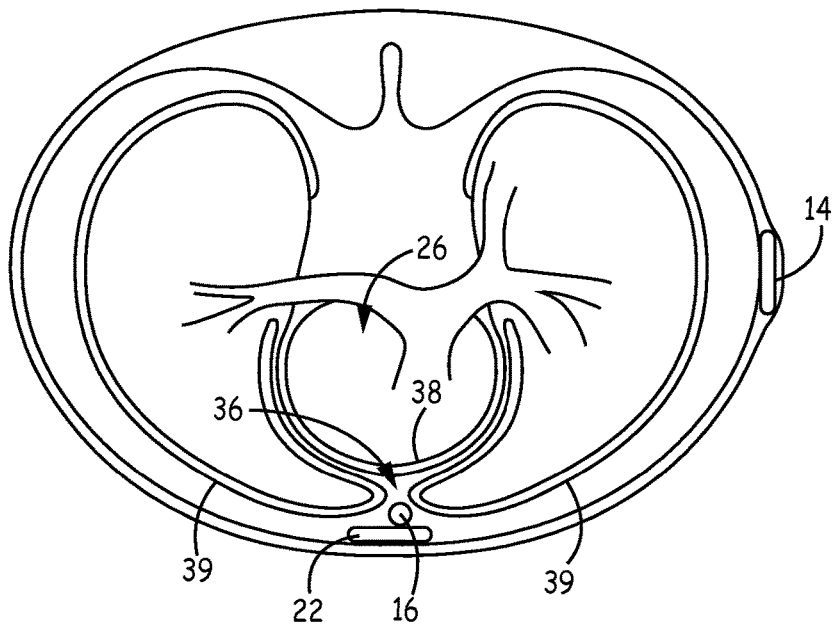
FIG. 2 is a transverse view of the patient in FIG. 1 depicting the defibrillation and sensing lead implanted in an alternate location.

In other instances, lead 16 may be implanted at other extravascular locations. As shown in a transverse view of patient 12 in FIG. 2, lead 16 may be implanted at least partially in a substernal location, e.g., between the ribcage 32 and/or sternum 22 and heart 26. In one such configuration, a proximal portion of lead 16 extends subcutaneously from ICD 14 toward sternum 22 (not seen in the transverse view of FIG. 2) and a distal portion of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26 and not above sternum 22 or ribcage.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and distal electrode coil 24 and distal sensing electrode 28.

Referring again to FIG. 1, lead 16 includes an elongated lead body 18 carrying electrodes 24, 28 and 30 located along the distal portion of the length of the lead body 18. Lead body 18 insulates one or more elongated electrical conductors (not illustrated) that extend from a respective electrode 24, 28 and 30 through the lead body 18 to a proximal connector (not shown) that is coupled to ICD 14. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy module or a sensing module, via connections in an ICD connector assembly 17 that includes a connector bore for receiving the proximal connector of lead 16 and associated electrical feedthroughs crossing ICD housing 15. The electrical conductors transmit therapy from a therapy module within ICD 14 to one or more of electrodes 24, 28, and 30, and transmit cardiac electrical signals from one or more of electrodes 24, 28, and 30 to the sensing module within ICD 14.

Defibrillation lead 16 is shown in FIG. 1 to include a defibrillation electrode 24, which may be an elongated coil electrode, along the distal portion of defibrillation lead 16. Defibrillation electrode 24 is located on lead 16 such that when ICD system 10 is implanted a therapy vector between defibrillation electrode 24 and a housing or can electrode 15 of ICD 14 is substantially through or across the ventricle(s) of heart 26.

Defibrillation lead 16 also includes one or more sensing electrodes 28 and 30, located toward the distal portion of defibrillation lead 16. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. ICD system 10 may sense electrical activity of heart 26 via one or more sensing vectors that include combinations of electrodes 28 and 30 and the housing or can electrode 15 of ICD 14. For example, ICD 14 may receive a subcutaneous ECG signal across a sensing vector between electrodes 28 and 30, a sensing vector between electrode 28 and the conductive housing or can electrode 15, a sensing vector between electrode 30 and the conductive housing or can electrode 15, or any combination of electrodes 28, 30 and the housing or can electrode 15. In some instances, ICD 14 may even sense cardiac electrical signals using a sensing vector that includes defibrillation electrode 24.

ICD 14 analyzes the electrical signals received from one or more of the sensing vectors described above to detect and treat shockable tachyarrhythmias, such as VT or VF. ICD 14 may deliver one or more cardioversion or defibrillation shocks via defibrillation electrode 24 in response to detecting VT or VF. ICD 14 may also provide pacing therapy, such as anti-tachycardia pacing (ATP) and/or post-shock pacing after a cardioversion or defibrillation shock when pacing capabilities are available. As described herein, ICD 14 analyzes the electrical signals received from one or more of the sensing vectors after delivery of a CV/DF shock to determine if a shockable rhythm is still present requiring an additional shock or if asystole or bradycardia is present requiring post-shock cardiac pacing.

ICD 14 includes a housing 15, also referred to herein as housing electrode or can electrode 15, which forms a hermetic seal that protects internal electronic components of ICD 14. The housing 15 may be formed of a conductive material, such as titanium, titanium alloy, or other conductive material to serve as an electrode. Housing 15 may function as a "can electrode" since the conductive housing or a portion thereof may be coupled to internal circuitry to be used as an indifferent or ground electrode during sensing or cardioversion/defibrillation shock delivery.

ICD 14 also includes connector assembly 17 (also referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this case, defibrillation lead 16 may extend subcutaneously from the device toward the manubrium of the sternum 22 and bend or turn and extend subcutaneously or substernally inferiorly from the manubrium of the sternum, substantially parallel with the sternum.

The techniques disclosed herein may be implemented in numerous ICD and electrode configurations that include one or more housing-based electrodes and/or one or more lead-based electrodes for enabling sensing of a cardiac electrical signal developed across one or more sensing vectors and for delivering electrical stimulation therapies to heart 26 including at least a shock therapy. The IMD system 10 is an extravascular IMD system because lead 16 is positioned in an extravascular location outside the blood vessels, heart 26 and pericardium 38. It is understood that while ICD 14 and lead 16 may be positioned between the skin and a muscle layer of the patient 12, ICD 14 and any associated leads could be positioned in any extravascular location of the patient, such as below a muscle layer or even within the thoracic cavity.

An external device 40 is shown in telemetric communication with ICD 14 by a communication link 42. External device may include a processor 52, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters and ECG signals retrieved from ICD 14. User interface 56 which may include a mouse, touch screen, key pad or the like to enable a user to interact with external device 40 to initiate a telemetry session with ICD 14 for retrieving data from and/or transmitting data to ICD 14. Telemetry unit 58 is configured for bidirectional communication with a telemetry module included in ICD 14 and is configured to operate in conjunction with processor 52 for sending and receiving data relating to ICD functions via communication link 42.

Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD 14 functions. For example, external device 40 may be used to program cardiac event sensing parameters such as parameters used to control a cardiac event sensing threshold according to a decay sequence as described below. External device 40 may be used to program ICD tachyarrhythmia detection parameters and criteria relating to the rate, intervals, and/or morphology of ECG cardiac event signals. External device 40 may also be used to program therapy control parameters, such as the shock energy used to terminate VT or VF. External device 40 may alternatively be embodied as a home monitor or hand held device.

Examples of other IMD systems in which the techniques disclosed herein could be implemented for post-shock sensing of cardiac events and detection of a shockable rhythm after a shock therapy are generally disclosed in U.S. Pat. No. 8,332,022 (Brown et al.) and U.S. Pat. No. 5,447,519 (Peterson), and U.S. Pat. No. 7,496,409 (Greenhut, et al.) all of which patents are incorporated herein by reference in their entirety.

Figure 3:
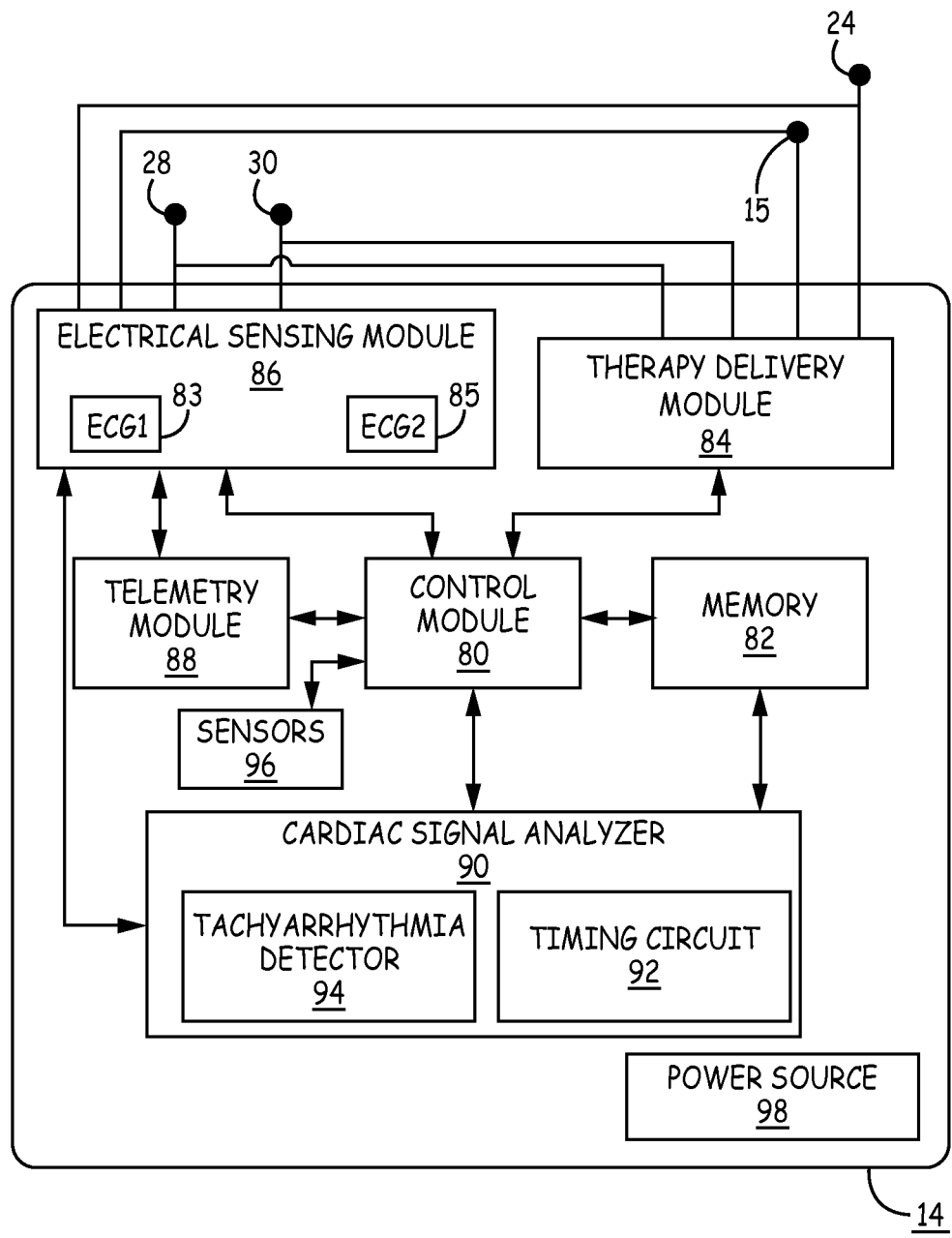
FIG. 3 is a schematic diagram of an ICD according to one embodiment.

FIG. 3 is a schematic diagram of ICD 14 according to one example. The electronic circuitry enclosed within housing 15 includes software, firmware and hardware that cooperatively monitor one or more ECG signals, determine when a cardioversion-defibrillation shock is necessary, and deliver prescribed cardioversion-defibrillation therapies. In some examples, ICD 14 may be coupled to a lead, such as lead 16, carrying electrodes, such as electrodes 24, 28 and 30, positioned in operative relation to the patient's heart for delivering cardiac pacing pulses, e.g., post-shock bradycardia pacing, in addition to shock therapies and may therefore include the capability to deliver low voltage pacing pulses as well as the high voltage shock pulses.

ICD 14 includes control module 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 may be implemented in control module 80 executing instructions stored in memory 82.

As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the device. Providing software, hardware, and/or firmware to accomplish the described functionality in the context of any modern IMD, given the disclosure herein, is within the abilities of one of skill in the art.

Control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 (shown in FIG. 1) and housing electrode 15, which may serve as a common or ground electrode.

Electrical sensing module 86 is selectively coupled to electrodes 28, 30 and housing electrode 15 in order to monitor electrical activity of the patient's heart. Electrical sensing module 86 may additionally be selectively coupled to electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing electrode 15. Sensing module 86 is shown to include two sensing channels 83 and 85 in the example of FIG. 3. Each sensing channel 83 and 85 may be configured to amplify and filter the ECG signal received from selected electrodes coupled to the respective sensing channel to improve the signal quality for sensing cardiac events, e.g., R-waves.

In one example, a first sensing channel 83 (ECG1) may be selectably configured to sense an ECG signal between sensing electrode 28 and ICD housing electrode 15 and a second sensing channel 85 (ECG2) may be selectably configured to sense an ECG signal between sensing electrode 30 and ICD housing electrode 15. In another example, one sensing channel 83 or 85 may receive an ECG signal using electrodes 28 and 30 and the other sensing channel 83 or 85 may receive an ECG signal using one of electrodes 28 and 30 paired with the housing electrode 15.

Each sensing channel 83 and 85 includes cardiac event detection circuitry for sensing cardiac events from the received ECG signal developed across the selected electrodes 24, 28, 30 or 15. Cardiac event sensing thresholds used by each sensing channel 83 and 85 are automatically adjusted according to sensing control parameters, which may be stored in memory 82. Control of the automatically-adjusted cardiac event sensing threshold for each sensing channel 83 and 85 may be implemented in control module 80. Each sensing channel 83 and 85 senses a cardiac event when the respective received ECG signal crosses the respective auto-adjusting cardiac event sensing threshold.

As described below, control module 80 may control the auto-adjusting cardiac event sensing threshold according to a post-shock decay sequence that includes a first post-shock decay sequence and a second post-shock decay sequence. The first post-shock decay sequence includes at least an initial sensing threshold amplitude and first post-shock decay rate. The first post-shock decay sequence is used to adjust an R-wave sensing threshold used by at least one or both sensing channels 83 and 85 until the first R-wave sense event signal is produced by the respective sensing channel after a shock pulse is delivered.

After the first, post-shock R-wave sense event signal is produced by a given sensing channel 83 or 85, the control module 80 controls the auto-adjusting R-wave sensing threshold according to a second post-shock decay sequence that is used for sensing R-waves during the remainder of a signal analysis segment. The second post-shock decay sequence includes at least an initial sensing threshold amplitude and at least one decay rate. The first post-shock decay sequence is controlled by a first set of sensing control parameters, and the second post-shock decay sequence is controlled by a second set of sensing control parameters different than the first set of sensing control parameters so that the first post-shock decay sequence is different than the second post-shock decay sequence. The cardiac event sensing thresholds for each sensing channel 83 and 85 may be controlled independently using the same or different post-shock decay sequence control parameters.

Each time the received ECG signal crosses the auto-adjusting sensing threshold for a given channel 83 or 85 outside a blanking interval, a cardiac event sense signal, also referred to herein as a "sense event signal" such as an "R-wave sense event signal," is produced and passed to control module 80 and/or cardiac signal analyzer 90. For example, R-wave sense event signals may be passed to tachyarrhythmia detector 94 and timing circuit 92 of cardiac signal analyzer 90 when a received ECG signal crosses the auto-adjusting R-wave sensing threshold for a given channel 83 or 85.

Sense event signals produced by sensing channel 83 or 85 during a post-shock ECG signal analysis time segment are counted to determine a total number of sense event signals. The total number or count of sense event signals may be used by cardiac signal analyzer 90 to estimate the post-shock cardiac cycle length. For example, when R-wave sense event signals are passed to cardiac signal analyzer 90, a ventricular cycle length estimate is determined from the total number or count of the R-wave sense event signals during a signal analysis time segment.

When two sensing channels are included in sensing module 86, two post-shock ventricular cycle length estimates may be determined by cardiac signal analyzer 90. One or both estimates may be used by tachyarrhythmia detector 94 for detecting a shockable rhythm post-shock. Additionally or alternatively, one or both estimates are used for controlling whether charging of high voltage capacitors included in therapy delivery module 84 is started at the expiration of the first post-shock ECG signal analysis time segment as described below.

Sensing module 86 may include an analog-to-digital converter for providing a digital ECG signal from one or all sensing channels 83 and 85 to control module 80 and/or cardiac signal analyzer 90. For example two ECG signals as described above may each be converted to a multi-bit digital signal by sensing module 86 and provided to tachyarrhythmia detector 94 for performing ECG morphology analysis. Analysis of the ECG signal morphology during one or more post-shock signal analysis time segments may be used to re-detect a shockable rhythm post-shock.

Cardiac signal analyzer 90 includes a tachyarrhythmia detector 94 for detecting and discriminating shockable and non-shockable rhythms. Cardiac signal analyzer 90 may further include a timing circuit 92 that includes various timers and/or counters for measuring time intervals, such as RR intervals, and setting time segments or windows such as morphology template windows, morphology analysis windows relative to R-wave sense event signals, post-shock cardiac signal analysis time segments, also referred to herein as "signal analysis segments," or for performing other timing related functions of cardiac signal analyzer 90 including synchronizing cardioversion shocks or other therapies delivered by therapy delivery module 84 with sensed cardiac events.

The timing of R-wave sense event signals received from sensing module 86 is used by timing circuit 94 to determine RR intervals between sense event signals. Tachyarrhythmia detector 94 may count RR intervals measured by timing circuit 92 that fall into different rate detection zones for determining a ventricular rate or performing other rate- or interval-based assessment for detecting ventricular tachyarrhythmia and discriminating shockable and non-shockable rhythms.

Examples of algorithms that may be performed by ICD 14 for detecting, discriminating and treating shockable rhythms, which may be adapted to include techniques described herein for sensing post-shock cardiac signals and responding thereto, are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable VT and VF.

Therapy delivery module 84 includes a high voltage (HV) therapy delivery module including one or more HV output capacitors and, in some instances, a low voltage therapy delivery module. When a malignant tachycardia is detected the HV capacitors are charged to a pre-programmed voltage level by a HV charging circuit. As described below, a decision to start charging HV output capacitors may be made by control module 80 in response to a cardiac cycle length estimate made by cardiac signal analyzer 90 at the expiration of a post-shock cardiac signal analysis segment. The estimated cycle length may be required to be equal to or less than a predefined VT or VF detection interval used by the shockable rhythm detection algorithm. In one example, if the estimated cycle length is 300 ms or less, capacitor charging will be started at the expiration of the post shock cardiac signal analysis segment. If additional signal analysis performed by cardiac signal analyzer 90 confirms re-detection of a shockable rhythm, HV output capacitor charging continues and another shock is delivered.

Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing electrode 15. Timing circuit 92 may be used to control R-wave synchronized shock pulses delivered by therapy delivery module 84.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

Certain steps in the performance of the post-shock sensing and post-shock rhythm detection described herein are cooperatively performed in control module 80 and cardiac signal analyzer 90 and stored detection criteria and other control parameters in memory 82. User-programmable control parameters may be programmed into memory 82 via telemetry module 88. Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40.

ECG episode data related to the detection of VT or VF and the delivery of a cardioversion or defibrillation shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable rhythms and delivering therapy.

Figure 4:
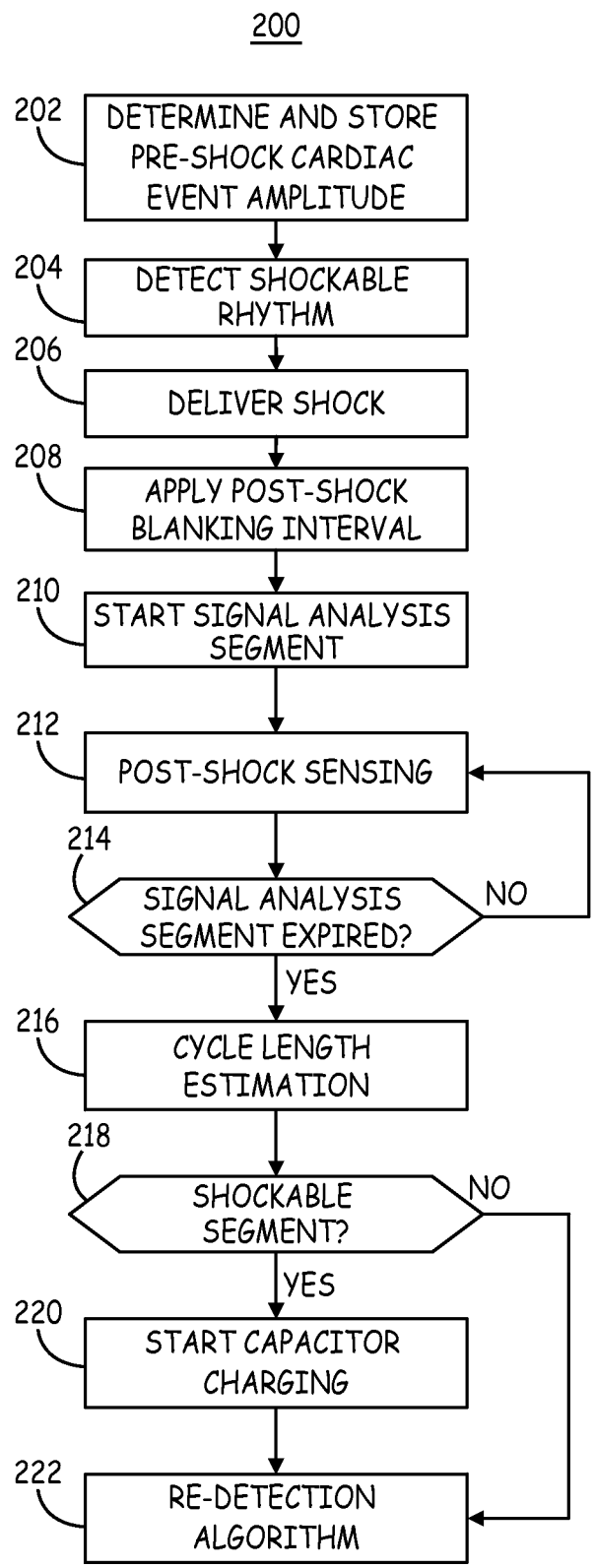
FIG. 4 is a flow chart of a method performed by an ICD for sensing cardiac events after delivering a CV/DF shock pulse.

FIG. 4 is a flow chart 200 of operations performed by ICD 14 for after delivering a cardioversion/defibrillation (CV/DF) shock pulse. The methods disclosed in conjunction with the flow charts and timing diagrams presented herein are directed toward controlling an R-wave sensing threshold for sensing R-waves after delivery of a ventricular CV/DF shock. It is contemplated, however, that techniques disclosed herein may be implemented for sensing R-waves in a ventricular chamber and/or P-waves in an atrial chamber following delivery of an atrial or ventricular CV/DF shock. Furthermore, aspects of the methods for controlling a post-shock cardiac event sensing threshold as disclosed herein may be implemented after delivering other types of therapeutic or non-therapeutic electrical stimulation, such as cardiac pacing for asystole, bradycardia or anti-tachycardia pacing or non-therapeutic induction shocks or stimulation pulses delivered to induce VT or VF. A post-shock decay sequence as described herein for controlling an auto-adjusting cardiac event sensing threshold may also be referred to as a "post-stimulation decay sequence" and should not be considered as being exclusively limited to sensing applications following a CV/DF shock pulse.

The processes described in conjunction with flow chart 200 and other flow charts and diagrams presented herein are generally described for a given sensing channel of sensing module 86. It is to be understood that the processes may be performed in conjunction with one sensing channel 83 or 85, but is more likely being performed concomitantly in conjunction with both sensing channels 83 and 85 in combination with control module 80 and cardiac signal analyzer 90.

Flow chart 200 is intended to illustrate the functional operation of ICD 14, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the ICD. Providing software, hardware, and/or firmware to accomplish the described functionality in the context of any modern ICD, given the disclosure herein, is within the abilities of one of skill in the art.

Methods described in conjunction with flow charts and diagrams presented herein may be implemented in a non-transitory computer-readable medium, e.g., included in memory 82, that includes instructions for causing a programmable processor to carry out the methods described. The instructions may be implemented as one or more software modules, which may be executed by themselves or in combination with other software.

At block 202, the ICD control module 80 determines a pre-shock (or more generally a pre-stimulation) cardiac event amplitude. For example, ICD control module 80 may determine a peak amplitude of a QRS morphology template determined by cardiac signal analyzer 90 and stored in memory 82. In some examples, a QRS morphology template is determined and stored for use in discriminating shockable and non-shockable rhythms. A QRS morphology template may be stored during a known intrinsic rhythm, e.g., during a known, non-paced sinus rhythm, and compared to a cardiac electrical signal during an unknown rhythm. If the signal during the unknown rhythm matches the template, the unknown rhythm is detected as the rhythm corresponding to the template, e.g., a non-shockable sinus or other supraventricular rhythm. If ICD 14 is configured to determine and store a QRS morphology template, a pre-shock R-wave amplitude may be determined from the QRS template, e.g., as a peak R-wave amplitude of a template of one or more intrinsically sensed heart beats originating in the atria in the absence of cardiac pacing. In the case of atrial sensing applications, ICD control module 80 may determine a peak amplitude of a P-wave morphology template determined by cardiac signal analyzer 90. The pre-shock cardiac event amplitude may be measured from a filtered cardiac electrical signal that is filtered using the same filtering characteristics (e.g., filter bandpass) used by the respective sensing channel 83 or 85 for sensing cardiac events. Methods that may be used for automatically generating a template of a non-paced R-wave from which a pre-shock cardiac event amplitude may be determined are generally disclosed in U.S. Pat. No. 6,745,068 (Koyrakh, et al.), incorporated herein by reference in its entirety.

In other examples, the pre-shock event amplitude may be determined from a peak amplitude of one or more cardiac events as they are sensed. The pre-shock event amplitude is determined to represent an expected cardiac event amplitude during a non-shockable rhythm in some examples. As such, the pre-shock event amplitude is typically determined during a non-shockable rhythm at block 202, not during a shockable rhythm detected immediately prior to delivering a shock. In other examples, a pre-shock event amplitude may be determined from cardiac events sensed just prior to detecting a shockable rhythm, which may be stored as a pre-episode signal sample. In some examples, a pre-shock event amplitude may be determined from cardiac events sensed during a shockable rhythm that is detected prior to delivering a shock.

The pre-shock event amplitude may be stored in memory 82 and may be updated whenever a QRS morphology template (or other template) from which it is derived is updated. If the pre-shock event amplitude is determined from cardiac events sensed prior to a shock therapy, the event amplitude may be updated on a regular periodic basis or as needed at block 202. For example, if the electrodes coupled to a given sensing channel 83 or 85 are changed, the pre-shock event amplitude is updated at block 202 to provide a relevant pre-shock event amplitude for a newly selected sensing vector. A pre-shock event amplitude may be updated after terminating a shockable rhythm, after anti-tachycardia pacing therapy or other therapy is delivered or a therapy adjustment is made, after ICD programming changes, or after any other ICD-related or other change, such as a prescription change, is made that may alter the amplitude of cardiac events being sensed by the sensing channels 83 and 85. Updates to the pre-shock event amplitude may be performed automatically by ICD 14 or triggered manually by a user interacting with external device 40.

At block 204, a shockable rhythm is detected by ICD 14. The initial shockable rhythm detection at block 204 occurs after a period of sinus rhythm, non-shockable supraventricular rhythm, or cardiac pacing. The shockable rhythm is detected using a detection algorithm implemented in ICD 14. The techniques disclosed herein for post-shock sensing and estimation of a post-shock cardiac cycle length are not limited to being practiced with a particular detection algorithm that is used for initial shockable rhythm detection, prior to delivering an initial CV/DF shock. Techniques disclosed in the above-incorporated patents may be used for initial shockable rhythm detection at block 204.

After a shockable rhythm is detected at block 204, a CV/DF shock is delivered at block 206. At block 208, a post-shock blanking interval is applied during which sensing module 86 is disabled from sensing cardiac electrical signals and producing cardiac event signals (or any produced cardiac event signals may be ignored by cardiac signal analyzer 90). The post-shock blanking interval is set to allow for post-shock electrode polarization recovery prior to re-enabling the sensing module 86 to sense cardiac events. The post-shock blanking interval is 1.5 seconds long in one example, but may be set to an interval greater than or less than 1.5 seconds depending on the time interval required for post-shock electrode polarization recovery in a given ICD system.

At block 210, control module 80 (or cardiac signal analyzer 90) starts a signal analysis segment upon expiration of the post-shock blanking interval. The signal analysis segment may be an n-second interval during which R-wave sensing is performed by sensing module 86 according to a post-shock sensing threshold sequence at block 212. In one example, the signal analysis segment is a three-second time interval started after expiration of post-shock blanking interval, e.g., 1.5 seconds after the shock in the example given above.

The sensing module 86 starts a post-shock sensing threshold decay sequence at block 212 at the onset of the signal analysis segment. The cardiac event sensing threshold used by each sensing channel 83 and 85 is adjusted by control module 80 according to sensing control parameters stored in memory 82 for controlling a post-shock sensing threshold decay sequence. The post-shock decay sequence is described below in conjunction with FIGS. 7 and 8. Each time the filtered and rectified cardiac electrical signal crosses the post-shock sensing threshold outside a blanking interval, a cardiac sense event signal, e.g., an R-wave sense event signal, is generated by the respective sensing channel 83 or 85. After each sensing threshold crossing, a blanking interval, typically between 150 and 180 ms is applied during which cardiac event sense signals are not produced by the sensing channels 83 and 85.

Cardiac signal analyzer 90 receives the R-wave sense event signals. Upon expiration of the signal analysis segment at block 214, the cardiac signal analyzer 90 estimates the post-shock cardiac event cycle length at block 216 based on the received sense event signals. Determining an estimated cycle length includes counting sense event signals produced during the post-shock signal analysis segment and estimating a cycle length based on the sense event signal count.

In one example, cardiac signal analyzer 90 receives R-wave sense event signals from each ECG sensing channel 83 and 85. For each channel, the cardiac signal analyzer 90 counts how many R-wave sense event signals are received during the signal analysis segment to obtain a total number or count of R-wave sense event signals for each channel 83 and 85. A ventricular cycle length is estimated based on the total number or count of R-wave sense event signals for each channel 83 and 85 as described below. Actual intervals between R-wave sense event signals need not be determined in some examples and an estimate may be made based on the total number of sense event signals.

The cycle length estimation performed at block 216 may include comparing the total number of R-wave sense event signals to one or more count thresholds or ranges. For example, the ventricular cycle length estimate is determined to be unknown if a threshold number of R-wave sense event signals is not received during the signal analysis segment. If a threshold number of R-wave sense event signals are received, each RR interval between two consecutive R-wave sense event signals is determined. The cycle length is estimated from the determined RR intervals. The cycle length may be estimated as the mean, median, or nth longest interval of all or a subset of the RR intervals determined during the signal analysis segment. Different methods may be used to determine the estimated cycle length depending on how many R-wave sense event signals are received during the signal analysis segment.

In an illustrative example, a threshold number of R-wave sense event signals required to estimate the post-shock ventricular cycle length is seven. If less than seven R-wave sense event signals are received from a given cardiac signal sensing channel of sensing module 86 during a three-second signal analysis segment, the ventricular cycle length estimate is "unknown." If at least seven but less than thirteen R-wave sense event signals are received from a given cardiac signal sensing channel 83 or 85, the RR intervals occurring between consecutive R-wave sense event signals are determined by cardiac signal analyzer 90. At least seven R-wave sense event signals results in at least six RR intervals that can be determined. Cardiac signal analyzer 90 orders the determined RR intervals from shortest to longest. The third longest RR interval is determined as the estimated post-shock ventricular cycle length for the signal analysis segment.

If more than thirteen R-wave sense event signals are received from a given sensing channel 83 or 85 during the signal analysis segment, at least twelve RR intervals can be determined. The RR intervals are ordered from shortest to longest and the post-ventricular cycle length is estimated as the mean of the $7^{th}$ to $10^{th}$ longest RR intervals for the signal analysis segment.

In other examples, different ranges of the total number of R-wave sense event signals counted during the signal analysis segment may be defined. The different ranges may be based at least in part on the duration of the signal analysis segment and the available size of memory buffers used to store RR intervals. Distinct methods for estimating the post-shock ventricular cycle length may be defined for each of the different ranges, such as "unknown", nth longest of the determined RR intervals, median of the determined RR intervals or median of the Nth through Mth longest intervals, mean of the determined RR intervals or mean of the Nth through Mth longest intervals, a mode of the intervals or subset of the intervals, or other parametric or non-parametric methods.

When more than one cardiac signal is being analyzed for post-shock sensing and rhythm detection, the cycle length estimate determined at block 216 for one cardiac signal sensing channel 83 or 85 may influence the estimate made for the other sensing channel 83 or 85, or the estimates for all channels may be used to determine a combined or overall estimate. For example, if two sensing channels 83 and 85 are being used and the estimate for one sensing channel is "unknown" due to less than a threshold count of R-wave sense event signals being received from that channel, an estimate determined for the other sensing channel may replace the "unknown" estimate for the first channel. In other words, if two sensing channels are used, the same estimate will be stored for both channels when the estimate for one channel is "unknown."

The ventricular cycle length estimate determined at block 216 is provided as input to a decision block 218 for determining if the signal analysis segment is a shockable segment. The signal analysis segment may be a shockable segment if the cycle length estimate meets a shockable rhythm criterion, e.g., less than 300 ms or another predefined VT or VF detection interval. Other shockable segment criteria besides a threshold requirement for the estimated cycle length may be applied at block 218. For example, gross morphology metrics may be determined using the sample points of the cardiac signal sampled across the n-second signal analysis segment, e.g., as generally disclosed in the above-referenced '842 patent (Zhang, et al.) and used in conjunction with the cycle length estimate for classifying the segment as shockable or non-shockable.

If the signal analysis segment is classified as a shockable segment based at least on a comparison of the cycle length estimate to shockable segment classification criteria, high voltage capacitor charging is started at block 220 by the therapy delivery module 84 under the control of control module 80. Classification of the first signal analysis segment following the post-shock blanking interval as a shockable segment causes capacitor charging to begin rapidly after an initial shock so that the ICD 14 is prepared to promptly deliver another shock if the initially detected shockable rhythm was not successfully terminated by the first shock (delivered at block 206).

In one example, the first signal analysis segment is at least three seconds long and a decision to start capacitor charging is made in response to classifying at least the first signal analysis segment as a shockable segment based on at least the cycle length estimation of first signal analysis segment. In another example, the first signal analysis segment is at least six seconds long, and the decision to start capacitor charging is made in response to classifying at least the first signal analysis segment as a shockable segment. In yet another example, at least two signal analysis segments may be required to be classified as shockable segments prior to starting capacitor charging at block 220. For example, if two consecutive three-second signal analysis segments following the post-shock blanking interval are both classified as shockable based on at least the respective cycle length estimation made for each segment, capacitor charging is started at block 220.

In some cases, the first signal analysis segment is an n-second segment, e.g., a six-second segment, over which the cycle length estimate is made based upon R-wave sense event signals produced during the entire n-second segment. Morphology analysis is performed over all or only a portion of the n-second segment that is less than n-seconds, e.g., the last three seconds of a six-second segment. The morphology analysis over the portion of the n-second segment may include analysis of single beats, e.g., single R-waves, and/or gross morphology that characterizes the cardiac signal over the entire portion of the signal analysis segment, which may include more than one R-wave. The portion over which the gross morphology analysis is performed is not necessarily defined based on the timing of an R-wave sense event signal. The gross morphology analysis may use all of the equally-spaced sample points acquired during the portion of the n-second segment to determine morphology metrics that are used to classify the segment as shockable or non-shockable. Examples of gross morphology metrics include a low slope content, normalized mean rectified amplitude, spectral width, and signal overall variability as disclosed in U.S. Pat. No. 8,301,233 (Zhang et al.), incorporated herein by reference in its entirety. If the segment is classified as a shockable segment at block 218 based on at least the cycle length estimation and optionally the morphology analysis, capacitor charging may be started at block 220. In some cases the decision to start capacitor charging at block 220 is based on the cycle length estimation for at least one signal analysis segment, and the decision to deliver a second shock is based on a combination of both cycle length estimation and morphology analysis of more than one signal analysis segment.

During capacitor charging (block 220), post-shock cardiac signal analysis continues according to an implemented shockable rhythm re-detection algorithm at block 222. In some examples, cardiac signal analyzer 90 continues to analyze n-second signal analysis segments of one or more cardiac signals. If at least x of y segments are classified as shockable segments, e.g., based on an estimated cycle length and/or gross morphology analysis, the high voltage capacitor charging is completed and another shock pulse is delivered according to programmed therapy control parameters. If shockable rhythm re-detection criteria are not met within a predetermined interval of time, the capacitor charging started at block 220 may be terminated. The capacitors may be discharged through a non-therapeutic load.

If the shockable rhythm is redetected and another shock pulse is delivered, the process of flow chart 200 may be repeated beginning at block 208 by starting another post-shock blanking interval and controlling the cardiac signal sensing threshold according to the post-shock decay sequence again. The post-shock decay sequence may be repeated as many times as shocks are delivered.

The parameters used to set and control the cardiac signal sensing threshold during the first, post-shock signal analysis segment are different than the parameters used to set and control the cardiac signal sensing threshold prior to an initial shock delivery, i.e., pre-shock. After the first post-shock signal analysis segment, the cardiac event sensing threshold used for sensing events and detecting a shockable rhythm subsequent to the first signal analysis segment may be automatically adjusted according to a different decay sequence than during the first, post-shock signal analysis segment. A unique cardiac event sensing threshold decay sequence may be used only during the first cardiac signal analysis segment post-shock for accurately and rapidly arriving at an estimated cardiac cycle length. The parameters used to automatically adjust the cardiac event sensing threshold during subsequent post-shock signal analysis segments may be different than the first post-shock decay sequence and may be the same or different than the parameters used to set and control the pre-shock decay sequence used to automatically adjust the sensing threshold prior to the initial shock delivery.

Figure 5:
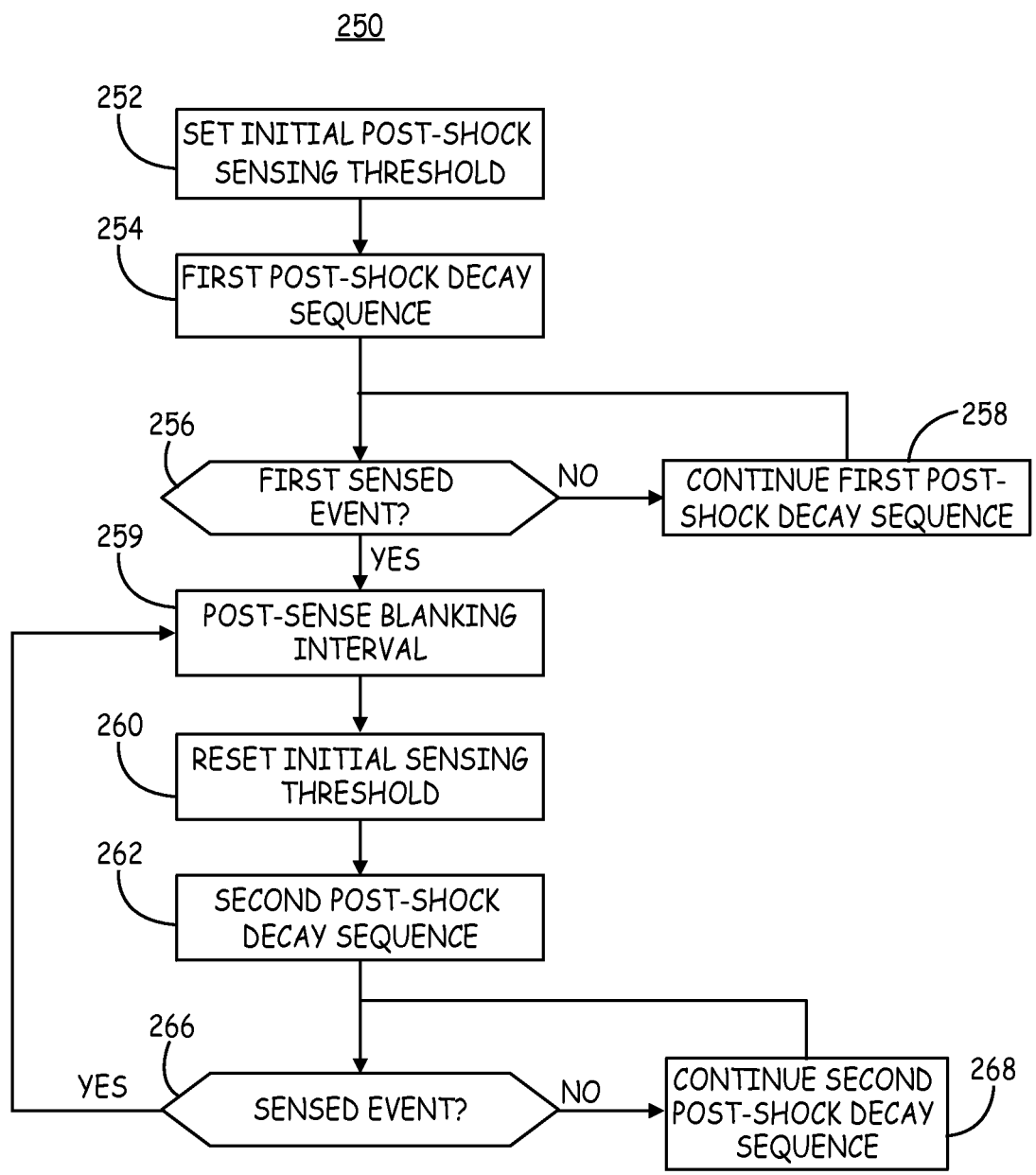
FIG. 5 is a flow chart of a method for setting and controlling a cardiac event sensing threshold post-shock according to one example.

FIG. 5 is a flow chart 250 of an example method for controlling a cardiac event sensing threshold used during the post-shock sensing performed by the ICD 14 in the flow chart 200 of FIG. 4. The techniques shown in FIG. 5 may be applied to each sensing channel 83 and 85 of sensing module 86 when multiple cardiac signals are being analyzed during a post-shock signal analysis segment. When a shock is delivered, a post-shock blanking interval is applied to the sensing module 86 after which the first post-shock cardiac signal analysis segment is started as described above in conjunction with blocks 208 and 210 of FIG. 4. The methods shown in FIG. 5 relate to the post-shock sensing performed at block 212 of FIG. 4.

Upon starting the signal analysis segment, the sensing module 86 begins post-shock sensing by setting the R-wave sensing threshold amplitude to an initial threshold at the immediate onset of the first post-shock signal analysis segment. In one example, the initial post-shock sensing threshold amplitude is set based on the pre-shock R-wave amplitude determined and stored at block 202 of FIG. 4. In an illustrative example, the initial threshold is set at block 252 to 30% of the R-wave amplitude stored in ICD memory 82, which may be the peak amplitude determined from a QRS morphology template generated during a supraventricular rhythm. When two sensing channels 83 and 85 are being used, a QRS morphology template may be stored for each sensing vector. An R-wave amplitude may be determined from each template and stored for the respective sensing vector. The initial post-shock sensing threshold is set for each respective sensing channel 83 and 85 based on the R-wave amplitude stored for the respective sensing vector.

At block 254, a first post-shock decay sequence is started and continues at block 258 until an R-wave is sensed at block 256. The first post-shock decay sequence results in an overall decay rate that is faster than a pre-shock decay sequence of the R-wave sensing threshold. The first post-shock decay sequence may include one or more decay rates and one or more step drops in the sensing threshold amplitude. One example of a first post-shock decay sequence is described below in conjunction with FIG. 7.

The first time the cardiac signal crosses the post-shock sensing threshold for a given sensing channel 83 or 85, a first post-shock R-wave is sensed, and an R-wave sense event signal is produced by the respective sensing channel 83 or 85. A post-sense blanking interval is applied at block 259, during which new events cannot be sensed but the maximum peak amplitude of the sensed event is determined.

After the post-sense blanking interval, e.g., 150 ms of blanking, a second post-shock decay sequence is started beginning with a new initial threshold amplitude set at block 260. The R-wave sensing threshold may be reset to a new initial threshold that is based on the peak amplitude determined during the post-sense blanking interval according to one example. The initial threshold amplitude decays according to the second post-shock decay sequence at block 262, which may be defined differently than the first post-shock decay sequence.

All events that are sensed during the signal analysis segment but after the first sensed R-wave are sensed using the second post-shock decay sequence. The second post-shock decay sequence starts decaying from the initial sensing threshold that is set at block 260 based on the sensed event peak amplitude determined during the post-sense blanking period immediately preceding the second post-shock decay sequence. rather than the stored pre-shock R-wave amplitude. The second post-shock decay sequence is different than the first post shock decay sequence and is used for sensing R-waves for the remainder of the cardiac signal analysis segment. The second post-shock decay sequence may include one or more decay rates and one or more step drops in sensing threshold.

If the signal analysis segment expires as determined at block 214 of FIG. 4, the cardiac signal analyzer 90 estimates the ventricular cycle length during the segment, classifies the segment as shockable or non-shockable, and may advance to a next signal analysis segment according to an implemented re-detection algorithm. It is recognized that in some cases the signal analysis segment could expire before the first event is sensed or before a threshold number of events are sensed (e.g., less than seven events) in which case the estimated cycle length is unknown.

As long as the signal analysis segment has not expired, the second decay sequence continues at block 268 until the cardiac signal crosses the R-wave sensing threshold that is decaying according to the second post-shock decay sequence. If the cardiac signal crosses the sensing threshold during the second post-shock decay sequence, an event is sensed at block 266. If the signal analysis segment has not expired, a post-sense blanking interval is applied at block 259 during which the peak amplitude of the sensed event may be determined for use in setting the next initial sensing threshold at block 260. The second post-shock decay sequence is restarted and repeated by the sensing module 86 each time an R-wave sense event signal is produced until the signal analysis segment expires.

In other examples, a predefined signal analysis segment is not required for implementing the first and second post-shock decay sequences. The first and second post-shock decay sequences may be utilized for sensing cardiac events after a post-shock blanking interval and continued for any desired post-shock sensing period that is not necessarily limited to one or more signal analysis segments. The sensed cardiac events may be used as they are sensed by cardiac signal analyzer 90 to determine a need for post-shock pacing or the need for another shock therapy, e.g., based on intervals measured between R-wave sense event signals.

Figure 6:
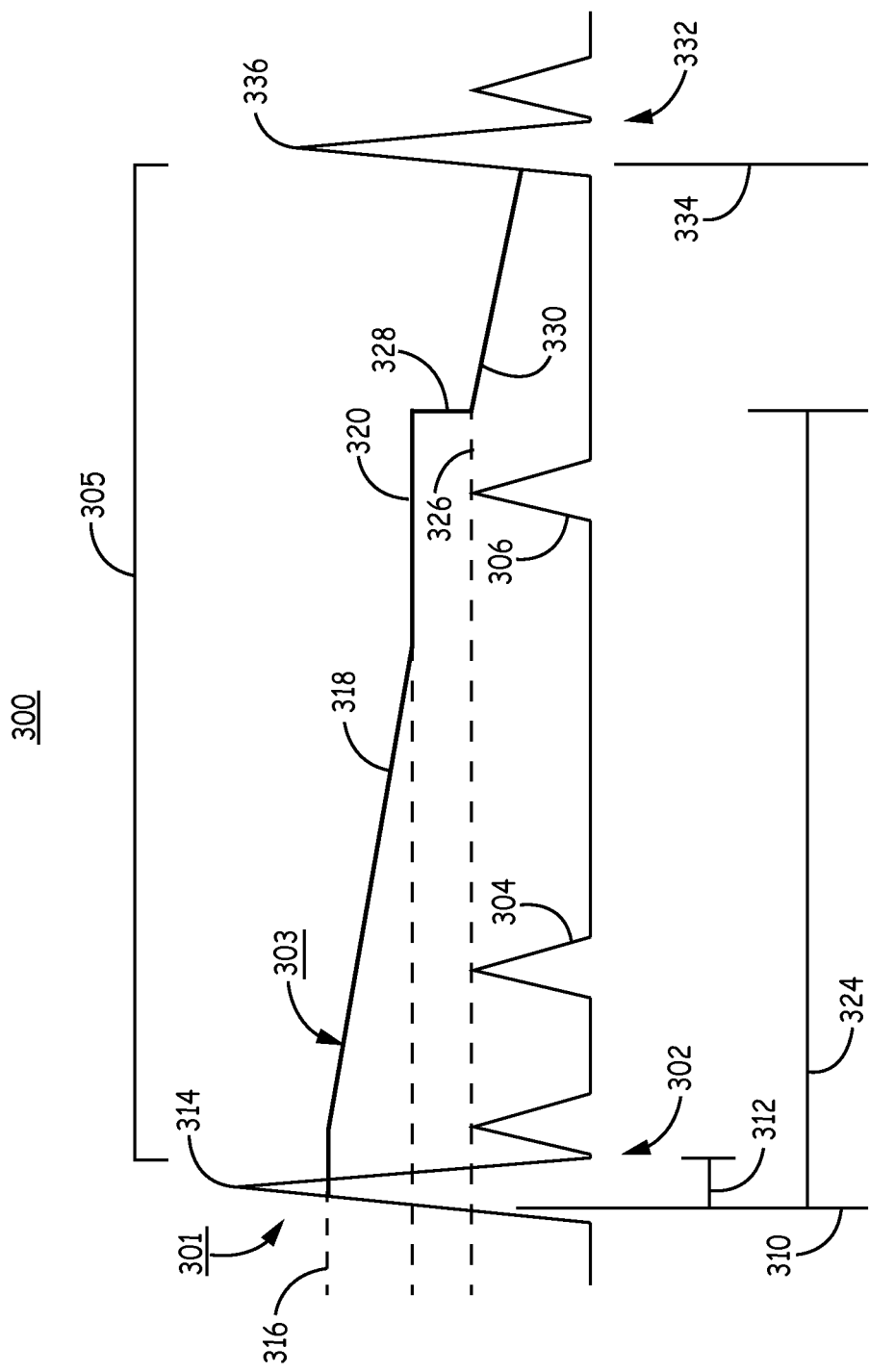
FIG. 6 is a diagram of a cardiac electrical signal and an automatically adjusted cardiac event sensing threshold prior to delivery of a shock.

FIG. 6 is a conceptual diagram 300 of a cardiac electrical signal 301, e.g., an ECG, received by ICD sensing module 86 and an automatically adjusted pre-shock R-wave sensing threshold 303. The cardiac electrical signal 301 includes a QRS complex 302, T-wave 304, P-wave 306 and a next QRS complex 332. The cardiac signal may be passed through a bandpass filter (e.g., passing 10 Hz to 32 Hz) and rectified so that only positive deflections remain as shown in FIG. 6. An R-wave sense event signal 310 is produced when the R-wave of the first QRS complex 302 crosses a sensing threshold (not illustrated). A post-sense blanking interval 312 is applied to the sensing module 86 after R-wave sense event signal 310. The post-sense blanking interval 312 is in the range of 150 ms to 180 ms in some examples, but may be set to longer or shorter intervals as needed to avoid sensing the same QRS complex 302 twice.

The R-wave peak amplitude 314 after the R-wave sense event signal 310 is determined, e.g., during the blanking interval 312, and used to set the initial amplitude 316 of the R-wave sensing threshold 303 during the succeeding cardiac cycle. After post-sense blanking interval 312, the R-wave sensing threshold 303 is applied according to a pre-shock decay sequence 305. The R-wave sensing threshold 303 begins at the initial amplitude 316 and decays at a first, pre-shock decay rate 318. The R-wave sensing threshold 303 decays at the first pre-shock decay rate 318 until it reaches an intermediate threshold amplitude 320, which may be a predetermined percentage of the peak amplitude 314 of the most recently sensed R-wave.

In one example, the pre-shock sensing threshold 303 has an initial amplitude 316 set to a first predetermined percentage, e.g., 60%, of the most recent R-wave peak amplitude 314. The pre-shock first decay rate 318 is set such that the sensing threshold 303 decays at a rate of 35% (of the peak R-wave amplitude 314) per second in the example shown. The first decay rate 318 is applied over a drop interval 324 which is a predetermined time interval. If the sensing threshold 303 reaches a predetermined intermediate amplitude 320 within the drop interval 324, the sensing threshold 303 is held at the predetermined amplitude 320 until the drop interval 324 expires. In one example, the predetermined intermediate amplitude 320 is 30% of the most recent R-wave peak amplitude 314.

The pre-shock drop interval 324 may be started when the R-wave sense event signal 310 is produced or upon expiration of blanking interval 312. The pre-shock drop interval 324 is 1.5 seconds in one example. The first decay rate 318, the predetermined intermediate amplitude 320, and the drop interval 324 are pre-shock sensing control parameters that are selected to prevent the R-wave sensing threshold 303 from falling below an expected amplitude of the T-wave 304 and P-wave 306, which could otherwise result in oversensing of T-waves and/or P-waves as false R-wave sense events. After the pre-shock drop interval 324 expires, the R-wave sensing threshold 303 is adjusted by a step-drop 328 to a second predetermined intermediate amplitude 326 of the R-wave peak amplitude 314. In one example, the second predetermined intermediate amplitude 326 is 10% of the R-wave peak amplitude 314.

After the step-drop 328, the R-wave sensing threshold 303 starts a second pre-shock decay rate 330. This second pre-shock decay rate 330 continues until the cardiac signal 301 crosses the R-wave sensing threshold 303, producing the next R-wave sense event signal 334, or until the R-wave sensing threshold 303 reaches a sensing threshold floor. The sensing threshold floor is a minimum sensing threshold amplitude, e.g., 25 µV or less. If the cardiac signal 301 does not cross the R-wave sensing threshold during the second decay rate 330, the R-wave sensing threshold will remain at the sensing floor until the cardiac signal 301 crosses the sensing floor (or until an escape interval expires resulting in a pacing pulse). The time interval from the first R-wave sense event signal 310 to the next R-wave sense event signal 334 is measured as an RR interval and used for detecting and discriminating shockable and non-shockable rhythms in accordance with an implemented detection algorithm. The next R-wave sense event signal 334 starts the next pre-shock blanking interval and next pre-shock drop interval (not illustrated though analogous to intervals 312 and 324 respectively). The R-wave peak amplitude 336 of the sensed QRS complex 332 is used to set the next initial R-wave sensing threshold of the next pre-shock decay sequence. It is recognized that a pre-shock R-wave sensing threshold 303 may be automatically adjusted according to a pre-shock decay sequence 305 that includes various criteria for setting at least the initial amplitude and one decay rate and may include one or more intermediate amplitudes, two or more decay rates, and one or more drop intervals. The example shown and described in conjunction with FIG. 6 is one illustrative example of a pre-shock decay sequence.

Figure 7:
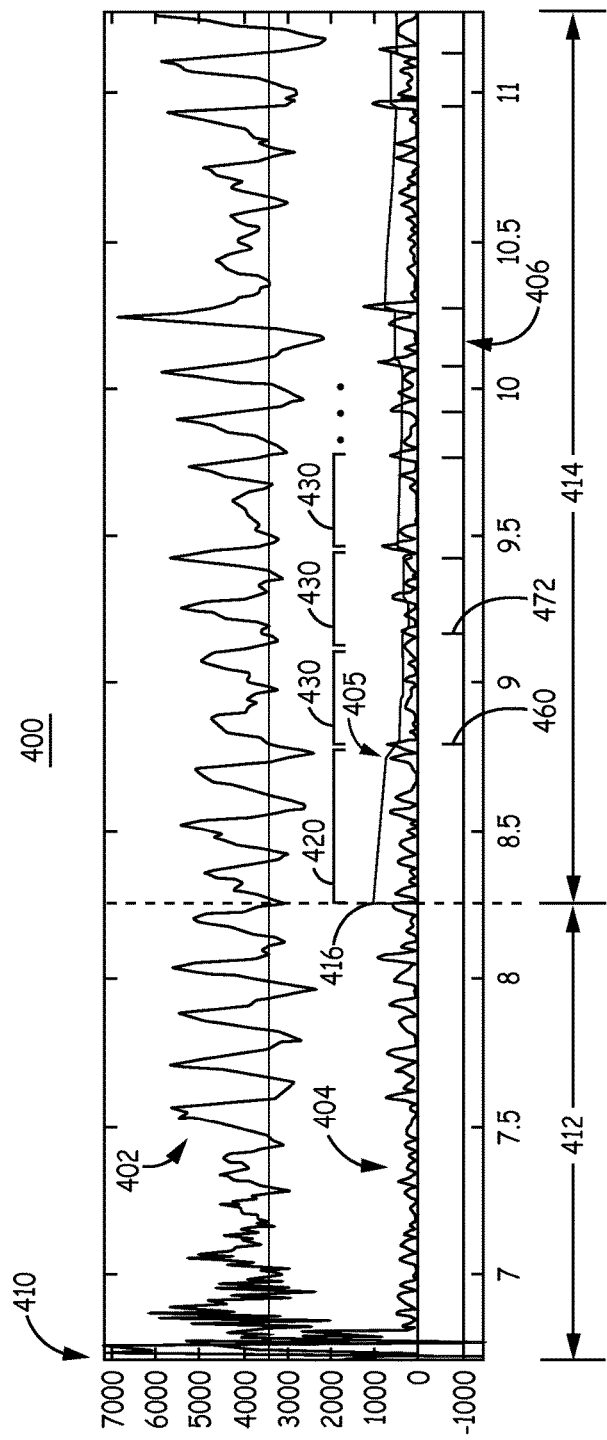
FIG. 7 is a diagram of a raw cardiac electrical signal, a filtered and rectified cardiac electrical signal, and cardiac event sensing threshold automatically adjusted post-shock delivery according to the disclosed techniques.
Figure 8:
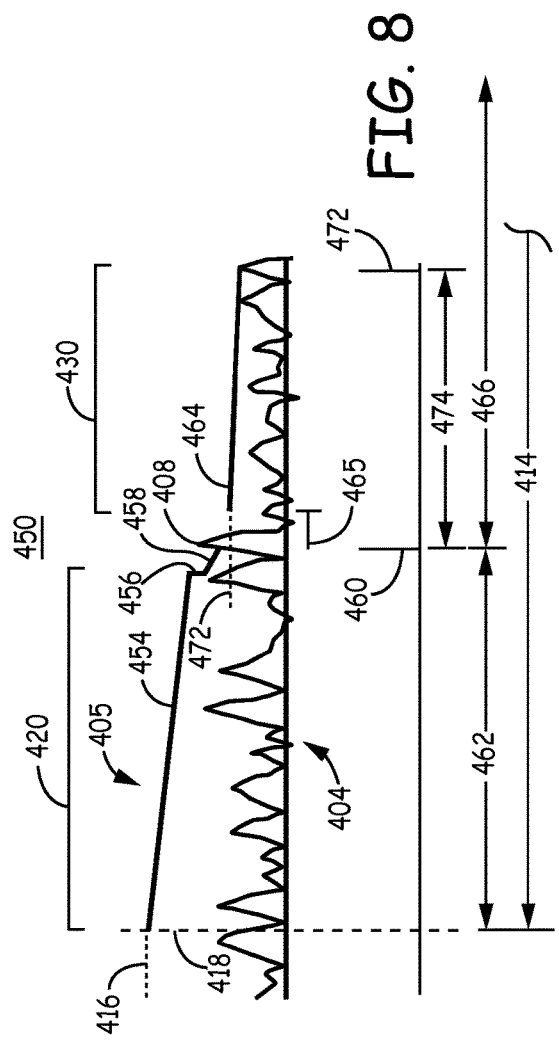
FIG. 8 is an enlarged view of a portion of the post-shock cardiac event sensing threshold shown in FIG. 7.

FIG. 7 is a diagram 400 of a raw cardiac electrical signal 402, a filtered and rectified cardiac electrical signal 404, a post-shock R-wave sensing threshold 405, and R-wave sense event signals 406. FIG. 8 is an enlarged view 450 of one example of the post-shock R-wave sensing threshold 405 shown in FIG. 7, beginning from the onset of a cardiac signal analysis segment 414.

A shock 410 is delivered in response an initial detection of a shockable rhythm. The raw cardiac signal 402 is filtered and rectified by the sensing module 86. A post-shock blanking interval 412 is applied to disable event sensing by the sensing module 86 during post-shock electrode polarization recovery. Post-shock blanking interval 412 is significantly longer than the pre-shock, post-sense blanking interval 312 shown in FIG. 6. Post-shock blanking interval 412 is set to 1.5 seconds in some examples.

A signal analysis segment 414 is started by cardiac signal analyzer 90 immediately upon expiration of the post-shock blanking interval 412. Signal analysis segment 414 is shown as a three-second segment in FIG. 7 but may be a longer or shorter segment in other examples. For example, segment 414 may be at least a six-second segment. The R-wave sensing threshold 405 during the first post-shock cardiac signal analysis segment 414 is adjusted by sensing module 86 according to a first post-shock decay sequence 420 and a second post-shock decay sequence 430. The first post-shock decay sequence 420 is defined by sensing control parameters that are unique and distinct compared to the pre-shock decay sequence 305 shown in FIG. 6 and compared to the post-shock decay sequence used in subsequent post-shock signal analysis segments (not illustrated) that occur after segment 414. Sensing control parameters used to set and adjust R-wave sensing threshold 405 during the first post-shock decay sequence may include an initial R-wave sensing threshold amplitude 416, one or more decay rates, one or more step drop intervals, and one or more intermediate sensing threshold amplitudes reached between changes in decay rates or after a step drop in sensing threshold amplitude.

For example, the R-wave sensing threshold 405 is set to initial sensing threshold amplitude 416 based on a stored pre-shock R-wave amplitude determined prior to shock 410.

As described above, the initial R-wave sensing threshold amplitude 416 may be set based on an R-wave amplitude of a supraventricular rhythm template stored for use in detecting and discriminating shockable and non-shockable rhythms. The initial R-wave sensing threshold amplitude 416 may be set to 30% or another predetermined percentage of the maximum peak R-wave amplitude of a sinus rhythm QRS morphology template in one example.

A maximum initial R-wave sensing threshold 416 may be predefined. If 30% (or other predetermined percentage) of the pre-shock R-wave amplitude determined and stored at block 202 of FIG. 4 is greater than the predefined maximum, the initial R-wave sensing threshold amplitude 416 is set to the maximum. In one example, the maximum initial R-wave sensing threshold amplitude 416 is less than 3 mV, e.g., in the range of 1.5 to 2.0 mV. In one example, the initial R-wave sensing threshold amplitude 416 is set to 1.74 mV or 30% of the maximum R-wave peak amplitude of a stored, sinus rhythm QRS morphology template, whichever is lower.

In the example shown, the post-shock R-wave sensing threshold 405 immediately begins to decay according to a first post-shock decay sequence 420 starting from the onset 418 of signal analysis segment 414. Alternatively, the post-shock R-wave sensing threshold 405 may be held constant for a predetermined interval of time prior to starting to decay. In one example, the first post-shock decay sequence 420 includes a first sequence decay rate 454, a step drop interval 462, a step drop 456 to an intermediate threshold amplitude, and a first sequence second decay rate 458. A crossing of the R-wave sensing threshold 405 during the first post shock decay sequence 420 results in the first post-shock R-wave sense event signal 460.

In one example, the first sequence decay rate 454 is a rate of 20% per second of the R-wave peak amplitude used to set the initial post-shock sensing threshold amplitude 416. The first sequence decay rate 454 is therefore based on the pre-shock cardiac event amplitude. The first sequence first decay rate 454 may be a slower decay rate than the first pre-shock decay rate 318 of the pre-shock sensing threshold 303, but the decay is likely to be starting from a lower initial threshold amplitude. The step drop interval 462 is 500 ms in one example, which is significantly shorter than the step drop interval 324 of the pre-shock decay sequence 305. Upon expiration of the drop interval 462, the post-shock R-wave sensing threshold 405 may be adjusted by a step drop 456 to an intermediate R-wave amplitude and starts a first sequence second decay rate 458.

While a small step drop 456 is shown at the expiration of the step drop interval 462 to clearly demark the first decay rate 454 and the second decay rate 458, the step drop 456 may only result in a change in decay rate without a step change in R-wave sensing threshold amplitude in some examples. When the initial sensing threshold amplitude 416 is set to 30% of a stored maximum peak R-wave amplitude and the first decay rate is 20% of the stored maximum peak R-wave amplitude per second, the post-shock R-wave sensing threshold 404 will reach 20% of the stored maximum peak R-wave amplitude in 500 ms. The intermediate threshold amplitude to which the sensing threshold 405 is adjusted to at step drop 456 may be set to 20% of the stored maximum peak R-wave amplitude. As a result, the step drop 456 is a net zero change in sensing threshold amplitude because the sensing threshold 405 has reached the intermediate amplitude at the expiration of the step drop interval 462. The first decay rate 454 is changed to the second decay rate 458 at the expiration of step drop interval 462.

The first sequence second decay rate 458 is a relatively high or steep decay rate and greater than the first sequence first decay rate 454. Second decay rate 458 may be greater than pre-shock decay rates 318 and 330. In one example, the second decay rate 458 during the first post-shock decay sequence 420 is 100% per second of the maximum peak R-wave amplitude used to set the initial sensing threshold amplitude 416. In this way, the initial amplitude 416, first decay rate 454, intermediate amplitude, and second decay rate 458 may all be based on the pre-shock R-wave amplitude.

An R-wave sense event signal 460 is produced when the filtered, rectified cardiac signal 404 crosses R-wave sensing threshold 405. In some instances, the second decay rate 458 may reach a sensing floor (not shown) before the cardiac signal crosses the R-wave sensing threshold 405. The sensing floor is a minimum sensing threshold amplitude that, if reached during the second decay rate, is held constant until the cardiac signal crosses the R-wave sensing threshold. The sensing floor may be 15 to 25 µV in some examples.

While first post-shock decay sequence 420 is described in the context of a shock pulse in the illustrative examples provided herein, it is contemplated that a cardiac event sensing threshold may be controlled according to a decay sequence following other types of electrical stimulation pulses, wherein the decay sequence includes at least one sensing control parameter that is based on a pre-stimulation cardiac event amplitude. The pre-stimulation cardiac event amplitude may be determined from a cardiac event template stored during a known cardiac rhythm as described above.

The post-stimulation decay sequence may include an initial amplitude based on the pre-stimulation cardiac event amplitude and may further include at least one decay rate and/or an intermediate amplitude based on the pre-stimulation cardiac event amplitude. Other examples of a post-stimulation decay sequence, such as a post-pace decay sequence following delivery of a transthoracic pacing pulse, are disclosed in U.S. patent application Ser. No. 14/519,251, incorporated herein by reference in its entirety.

A decay sequence based at least in part on a pre-stimulation cardiac event amplitude may be used to control cardiac event sensing following an electrical stimulation pulse that is a cardiac pacing pulse delivered for treating asystole, bradycardia, or tachycardia; a shock for treating atrial or ventricular tachyarrhythmia; a shock or other stimulation pulse delivered to induce tachyarrhythmia during ICD testing, or any other electrical stimulation pulse. The stimulation pulse may be a relatively large amplitude pulse, e.g., delivered transthoracically using extracardiac electrodes such as the suprasternal or substernal electrodes 24, 28 and 30 shown in FIGS. 1 and 2. Transthoracic stimulation pulses are relatively higher in energy than cardiac stimulation pulses that are delivered using electrodes that are in close proximity or direct contact with the myocardium.

The post-shock decay sequence 420 or more generally any post-stimulation decay sequence that is based at least in part on a pre-stimulation cardiac event amplitude may be used following any large stimulation pulse after which rapid recovery of sensing cardiac electrical activity is required, particularly low amplitude cardiac activity. The post-stimulation decay sequence, which may be used in combination with post-sense decay sequence 552 after delivery of an electrical stimulation pulse, may be used any time discrimination between fine VF and asystole is required for controlling appropriate therapy delivery (e.g., a shock vs. pacing).

After the first post-shock R-wave sense event signal 460 is produced, a post-sense blanking interval 465 is applied, and the R-wave sensing threshold 405 is automatically adjusted according to a second post-shock decay sequence 430. The second post-shock decay sequence 430 starts with an initial R-wave sensing threshold amplitude 472 that is based on the maximum peak R-wave amplitude 408 determined following the R-wave sense event signal 460, e.g., during post-sense blanking interval 465. The initial R-wave sensing threshold amplitude 472 may be defined as a percentage of the maximum peak R-wave amplitude 408. In some examples, the initial R-wave sensing threshold amplitude 472 is set in the same manner as the pre-shock initial R-wave sensing threshold amplitude 316, e.g., 60% of the maximum peak amplitude of the most recent sensed event.

The second post-shock decay sequence 430 includes a first decay rate 464, a step drop interval 466, and a second decay rate (not illustrated). The first decay rate 464, an intermediate amplitude adjusted to upon expiration of the step drop interval 466, and the second decay rate may be defined in the same manner as the pre-shock sensing threshold decay sequence 305. The step drop interval 466, however, is shorter than the step drop interval 324 of the pre-shock sensing decay sequence 305. Step drop interval 466 may be at least as long as the step drop interval 462 of the first post-shock decay sequence 420. In one example, step drop interval 466 is 700 ms. The filtered, rectified cardiac signal 404 crosses the R-wave sensing threshold 405 during the second post-shock decay sequence 430 before the step drop interval 466 is expired in the example shown, and an R-wave sense event signal 472 is produced.

The second post-shock decay sequence 430 is repeated (as indicated in FIG. 7) in response to each R-wave sensed event signal 406 for the remaining time of the signal analysis segment 414. As each event is sensed, the amplitude of R-wave sensing threshold 405 is reset to a predetermined percentage of the peak amplitude of the sensed event and decays therefrom at the second sequence first decay rate 464, drops to an intermediate sensing threshold amplitude after the drop interval 466, and continues to decay at a second sequence second decay rate (not illustrated) until the next cardiac signal crossing of the R-wave sensing threshold 405. Other than the second sequence drop interval 466, the sensing control parameters used to control the second post-shock decay sequence 430, including setting the initial sensing threshold amplitude 472, the first decay rate 464, the intermediate sensing threshold amplitude (not illustrated) and the second decay rate (not illustrated) may be identical to the pre-shock decay sequence 305 as described in conjunction with FIG. 6.

The first-occurring R-wave sense event signal 460 and the next R-wave sense event signal 472 are used to determine an RR interval 474. At the end of signal analysis segment 414, e.g., 4.5 seconds post shock, the cardiac signal analyzer 90 estimates the ventricular cycle length based on the total number of R-wave sense event signals 406 received and counted by cardiac signal analyzer 90 during the signal analysis segment 414. Estimating the ventricular cycle length may include determining RR intervals between the R-wave sense event signals 406.

At the expiration of the signal analysis segment 414, a new segment analysis segment may be started according to the shockable rhythm re-detection algorithm implemented in IMD 14. Sensing of R-waves during any subsequent signal analysis segments may continue according to the second post-shock decay sequence 430. The first post-shock decay sequence 420, therefore, may be used a single time at the onset 418 of the first-occurring post-shock signal analysis segment 414.

At the expiration of signal analysis segment 414, the cardiac signal analyzer 90 determines if segment 114 is a shockable segment in response to at least the ventricular cycle length estimate. If signal analysis segment 414 is classified as a shockable segment, control module 80 starts HV output capacitor charging in some examples. Capacitor charging may be started while a shockable rhythm detection algorithm is operating to re-detect a shockable rhythm post-shock.

Capacitor charging may be started at the expiration of signal analysis segment 414 in response to a shockable segment classification based on at least the cycle length estimation made for segment 414. Alternatively, the decision to start capacitor charging may be made based on the classification of more than one signal analysis segment, for example at least two signal analysis segments or based on at least the cycle length estimation made for each of at least two signal analysis segments.

Thus, a method and apparatus for controlling ICD functions after delivery of a CV/DF shock have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method comprising:
   determining a pre-shock cardiac event amplitude;
   delivering an electrical shock to a heart of a patient, wherein the electrical shock is delivered to the heart via a plurality of electrodes; and
   adjusting, by a medical device and responsive to delivering the electrical shock, a cardiac sensing threshold to decay from an initial amplitude at a post-shock decay rate, wherein the post-shock decay rate is based on the pre-shock cardiac event amplitude.

2. The method of claim 1, wherein adjusting the cardiac sensing threshold includes:
   setting the initial amplitude of the cardiac sensing threshold.

3. The method of claim 2, wherein the initial amplitude is based on the pre-shock cardiac event amplitude.

4. The method of claim 1, the method further comprising:
   identifying, prior to delivering the electrical shock and based on the cardiac sensing threshold, pre-shock cardiac events during a pre-shock drop interval.

5. The method of claim 4, wherein delivering the electrical shock to the heart of the patient includes:
   delivering the electrical shock in response to the pre-shock cardiac events satisfying a therapy delivery criterion.

6. The method of claim 4, further comprising:
   adjusting, by the medical device and prior to delivering the electrical shock, the cardiac sensing threshold to decay at a pre-shock decay rate during the pre-shock drop interval.

7. The method of claim 4, wherein the post-shock decay rate is a first post-shock decay rate, wherein the cardiac sensing threshold decays at the first post-shock decay rate during a first post-shock drop interval, and wherein adjusting the cardiac sensing threshold includes:

adjusting the cardiac sensing threshold to decay at a second post-shock decay rate during a second post-shock drop interval that follows the first post-shock drop interval.

8. The method of claim 7, wherein the second post-shock decay rate is based on the pre-shock cardiac event amplitude.

9. The method of claim 7, wherein the second post-shock drop interval is longer than the first post-shock drop interval and shorter than the pre-shock drop interval.

10. The method of claim 1, wherein the post-shock decay rate is a first post-shock decay rate, the method further comprising:
   identifying, by the medical device and based on the cardiac sensing threshold, post-shock cardiac events, including at least one post-shock cardiac electrical signal crossing the cardiac sensing threshold; and
   adjusting, by the medical device and in response to identifying the post-shock cardiac events, the cardiac sensing threshold to decay at a second post-shock decay rate.

11. The method of claim 10, wherein the second post-shock decay rate is based on the pre-shock cardiac event amplitude.

12. The method of claim 1, wherein the electrical shock is at least 10 Joules.

13. A medical device comprising:
   sensing circuitry configured to detect cardiac events of a heart of a patient using a cardiac sensing threshold;
   therapy delivery circuitry configured to deliver an electrical shock to the heart via a plurality of electrodes coupled to the medical device; and
   processing circuitry configured to perform operations comprising:
      determining a pre-shock cardiac event amplitude; and
      responsive to delivering the electrical shock, adjusting the cardiac sensing threshold to decay from an initial amplitude at a post-shock decay rate, wherein the post-shock decay rate is based on the pre-shock cardiac event amplitude.

14. The medical device of claim 13, wherein adjusting the cardiac sensing threshold includes:
   setting the initial amplitude of the cardiac sensing threshold.

15. The medical device of claim 14, wherein the initial amplitude is based on the pre-shock cardiac event amplitude.

16. The medical device of claim 13, wherein the processing circuitry is further configured to perform operations comprising:
   identifying, prior to delivering the electrical shock and based on the cardiac sensing threshold, pre-shock cardiac events during a pre-shock drop interval.

17. The medical device of claim 16, wherein the processing circuitry is further configured to perform operations comprising:
   controlling the therapy delivery circuitry to deliver the electrical shock in response to the pre-shock cardiac events satisfying a therapy delivery criterion.

18. The medical device of claim 16, wherein the processing circuitry is further configured to perform operations comprising:
   adjusting, prior to the delivery of the electrical shock, the cardiac sensing threshold to decay at a pre-shock decay rate during the pre-shock drop interval.

19. The medical device of claim 16, wherein the post-shock decay rate is a first post-shock decay rate, wherein the cardiac sensing threshold decays at the first post-shock decay rate during a first post-shock drop interval, and wherein adjusting the cardiac sensing threshold includes:
   adjusting the cardiac sensing threshold to decay at a second post-shock decay rate during a second post-shock drop interval that follows the first post-shock drop interval.

20. A non-transitory computer-readable storage medium comprising instructions that, when executed, configure processing circuitry of a medical device to:
   determine a pre-shock cardiac event amplitude;
   sense delivery of an electrical shock to a heart of a patient; and
   adjust, responsive to delivering the electrical shock, a cardiac sensing threshold to decay from an initial amplitude at a post-shock decay rate, wherein the post-shock decay rate is based on the pre-shock cardiac event amplitude.

* * * * *